United States Patent [19]

Black et al.

[11] 4,221,962
[45] Sep. 9, 1980

[54] FIBER-OPTIC MOISTURE SENSOR FOR COMPOSITE STRUCTURES

[75] Inventors: Gregory T. Black, Los Angeles; Robert A. Johnson, Garden Grove, both of Calif.

[73] Assignee: Northrop Corporation, Los Angeles, Calif.

[21] Appl. No.: 899,222

[22] Filed: Apr. 24, 1978

[51] Int. Cl.² ............................................. G02B 5/14
[52] U.S. Cl. ........................................ 250/227; 73/73; 356/133
[58] Field of Search ............. 73/73; 356/133, 135, 356/136, 137; 350/96.10; 250/227, 597

[56] References Cited

U.S. PATENT DOCUMENTS

| 2,359,787 | 10/1944 | Peters et al. | 177/311 |
| 2,740,032 | 3/1956 | Bouyoucos | 201/63 |
| 2,977,842 | 4/1961 | Duke | 356/133 |
| 3,433,570 | 3/1969 | Hansen | 356/128 |
| 3,528,278 | 9/1970 | Sterling | 73/17 |
| 3,540,025 | 11/1970 | Levin et al. | 340/234 |
| 3,550,439 | 12/1970 | Hollies et al. | 73/73 |
| 3,680,364 | 8/1972 | Carrier | 73/73 |

Primary Examiner—David C. Nelms
Attorney, Agent, or Firm—Willard M. Graham

[57] ABSTRACT

A radiation carrier such as an optical glass fiber is embedded in a body of material such as a laminated composite panel with the free ends of the fiber extending to or beyond the edges of the structure so that radiation such as light can be directed through one end of the carrier and measured at the other end thereof, to monitor and detect the presence of moisture in the interior of the structure.

6 Claims, 5 Drawing Figures

FIBER-OPTIC MOISTURE SENSOR FOR COMPOSITE STRUCTURES

BACKGROUND OF THE INVENTION

1. Field of the Invention

The future of composites is now well established. Composite materials such as glass-epoxy, graphite-epoxy, boron-epoxy, etc., are replacing metal and other conventional materials in the manufacture of aircraft at a rapidly accelerating rate, and also offer a largely untapped potential in an ever-expanding variety of products.

As an example, in the manufacture of the forward section of the Northrop YF-17 aircraft, the use of graphite composites reduced weight by 40%, and costs by 30% compared to the all-metal design for the same assembly. Moreover, the all-metal fuselage section of the aircraft required 1300 parts and 20 subassemblies whereas only 260 parts and 10 subassemblies were required in an identical section fabricated of composites.

One troublesome problem that has been encountered in the manufacture of composite assemblies such as, for example, laminated panel sections, is the intrusion of moisture into the cured matrix. Since moisture in any measurable amount may destroy the integrity of the structure, it is of the utmost importance to detect its presence so that remedial steps can be taken to correct the problem.

2. Description of the Prior Art

There are known methods and apparatus for detecting the presence of moisture in the interior of various materials and compostions, and the exterior as well.

U.S. Pat. No. 2,359,787 (Peters et al), for example, discloses a prism mounted in an aircraft wing with one of its faces flush with an opening in the wing skin and exposed to light. The variation of the reflection of light on the prism face is sensed by a photoelectric cell to detect the presence of ice on the wing. U.S. Pat. No. 3,540,025 (Levin et al) discloses a similar ice detector which also automatically actuates a heating system to melt the ice, when its presence is detected.

Apparatus employing prisms and glass rods are described in U.S. Pat. Nos. 3,528,278 (Sterling) and 3,433,570 (Hansen), respectively, for detecting the presence of vapor or other gaseous media in a confined environment.

Other prior known apparatus such as hygrometers for detecting the presence of water in diverse materials including soil, are disclosed in U.S. Pat. Nos. 2,740,032 (Bouyoucos), 3,550,439 (Hollies et al), and 3,680,364 (Carrier).

None of the prior methods or means, however, are suitable for detecting the presence of moisture in laminated composite structures, primarily from the standpoint of adaptability, complexity, and cost.

while it is possible that more pertinent prior art exists, Applicants' search is believed to have been conducted with a conscientious effort to locate and evaluate the most relevent art available at the time, but the statement is not to be construed as a representation that no more pertinent art exists.

SUMMARY OF THE INVENTION

A length of radiation carrier such as optical glass in filament or fiber form, is sandwiched during lay-up between the plies or layers of composite material forming a laminated panel or structure, the carrier subsequently being cured in situ in the structure.

The free ends of the radiation carrier are left to extend to or beyond the edges of the structure so that radiation can be passed through the fiber and out the other end into suitable radiation measuring means. Moisture, having a different index of refraction than the composite material surrounding the carrier will reflect, absorb, and/or attenuate the radiation travelling through the carrier, thereby yielding, by its quantum or frequency shift, a measurable indication of the presence of moisture. Radiation, as referred to herein, means electromagnetic radiation of a suitable frequency or frequency band for passage through a carrier to interact with the carrier surface. An example of this would be visible light passing through an optical fiber. This invention is not, however, limited to radiation in the visible light range.

It is a primary object of our invention to provide a simple, inexpensive moisture monitoring and detecting method that is ideally suited to use in evaluating composite parts. structures, and assemblies. It is a further object of our invention to provide a means for detecting moisture that can be permanently embedded in a body of material without appreciably affecting its structural properties.

Other objects and advantages inherent in our invention will readily be seen with reference to the ensuing specification and drawing.

DESCRIPTION OF THE PREFERRED EMBODIMENTS

Figure 1:
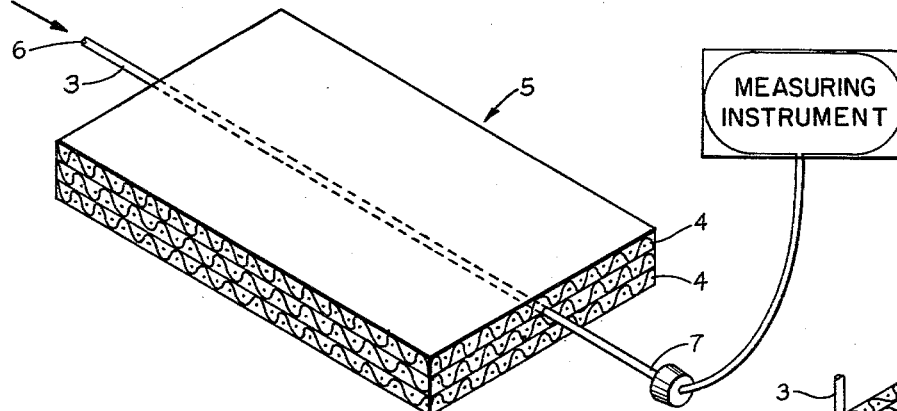
FIG. 1 shows a perspective view in cross-section showing a flat laminated panel formed of composite plies, with a radiation carrier sandwiched thereinbetween.

As shown in FIG. 1, a radiation carrier 3 such as an optical filament, rod, or fiber is sandwiched between plies or layers 4 of a composite material such as fiberglass, graphite, or boron cloth impregnated with an epoxy resin or the like, forming a flat panel structure 5. Such combinations are also known as laminates or matrix systems, and all such combinations are within the purview of the invention disclosed herein.

The free ends 6 and 7 of the light carrier 3 are left to extend to, i.e., flush with, or out of each side or end of the structure 5 as shown. On one end 6 of the carrier 3 a radiation beam, from any convenient source (not shown), is injected into the carrier 3, the beam travelling through the carrier to emerge from the other end 7 thereof where it is measured by a suitable radiation measuring instrument such as a photoelectric cell in (shown in FIG. 1) for example. The amount of attenuation, or frequency shift of the radiation, due to the presence of moisture can thus be detected and measured after the composite structure is cured, and thereafter during its full service life.

It will be understood that as many radiation carriers as are deemed necessary can be provided in any given structure, i.e., between all plies and layers if desired, since the strength and modulus of the fiber optic material, along with its extremely small diameter, is completely compatible with composite materials, and will not appreciably weaken the structure.

Figure 2:
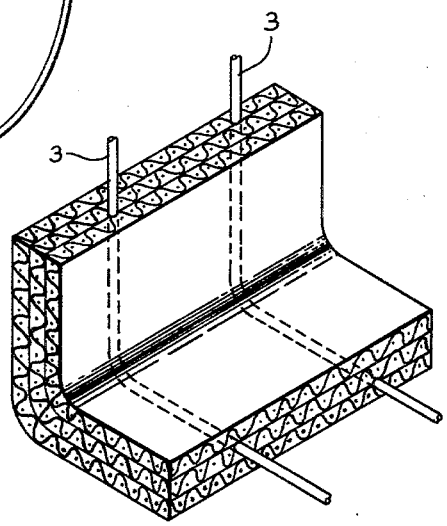
FIG. 2 shows a perspective view of a substantially right-angled member incorporating the radiation carrier of the present invention.
Figure 3:
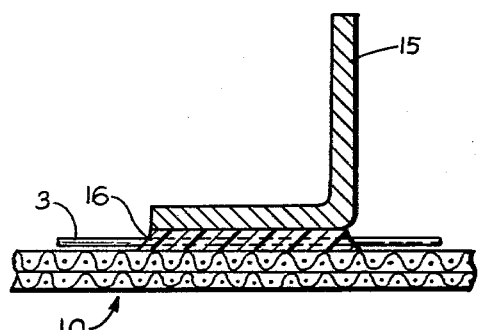
FIG. 3 is a magnified fragmentary side elevational view of a typical assembly wherein a bonded joint formed between two components is provided with a radiation carrier to detect the presence of moisture therein.

It is well known that optical filaments or fibers or other radiation carriers will conduct radiation around curves or bends as shown in FIG. 2, and also can be employed, for example, in a adhesive-bonded joint formed between two separate structures. FIG. 3 shows a laminated panel 10 such as an aircraft skin reinforced by a right-angled rib member 15, the panel and rib being bonded together with a high strength adhesive 16. One or the other of the members, the reinforcing rib 15, for example, may be fabricated of a conventional material such as metal, aluminum for example. Moisture penetration into the joint bond will degrade the strength of the bond and catastrophic failure of the joint may ultimately occur. The presence of moisture can be monitored and detected by embedding one or more lengths of optical fiber or other radiation carrier in the adhesive bond between the two structural components in the same manner illustrated in FIG. 1. The radiation attenuation characteristics in the bond material or adhesive can be predicted with the same degree of accuracy as in a composite laminate.

Figure 4:
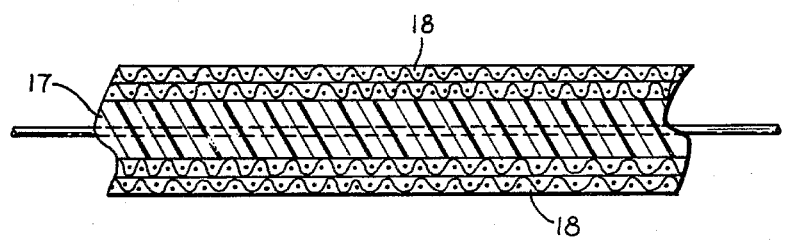
FIG. 4 is a cross-sectional view of a composite sandwich structure having a low density core incorporating the invention.

Composite sandwich structures employing high-strength, light-weight cores or plugs such as that shown in FIG. 4 are commonly used, the core material 17 being rigidized foamed polyurethane or the like, bonded on each side thereof to composite plies or sheets, or metal sheets, etc., 18. The radiation carrier 3 is embedded in the core material 17 and can thus be employed in accordance with the present invention, to detect the presence of moisture therein.

Figure 5:
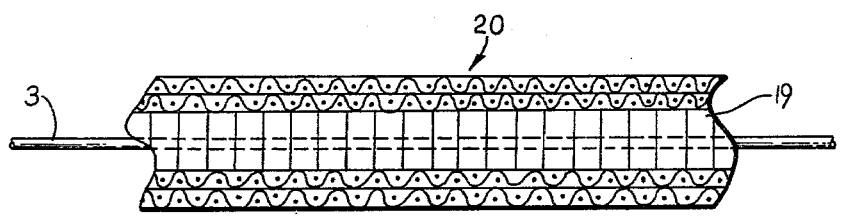
FIG. 5 is a cross-sectional view of a sandwich structure having a cellular core incorporating the invention.

Moreover, composite sandwich structures employing a honeycomb core 19, similar to the panel 20 shown in FIG. 5, can be provided with the radiation carrier 3, in accordance with the invention, to detect the presence of moisture within the cells.

While we have described our method in particular detail with respect to composite panel structures, it will readily be seen that our method can be used to detect the intrusion of moisture into solid bodies of material as well as bodies of laminated construction, and deem such uses as will occur to those skilled in the art to fall within the scope and spirit of our invention as set forth in the appended claims.

We claim:

1. A method of monitoring and detecting the intrusion of moisture into a body of a fully cured laminated composite structure, comprising:
   a. embedding and curing a radiation carrier inside said body of said composite structure, said radiation carrier having at least two finite ends extending to the edge of or out of said body of composite structure,
   b. injecting radiation into one end of said carrier, said radiation passing therethrough to emerge from the other end thereof, and
   c. measuring the radiation emerging from said other end of said carrier.

2. The method according to claim 1 wherein said body of laminated composite structure is substantially solid.

3. The method according to claim 1 wherein said body of laminated composite structure is laminar.

4. The method according to claim 1 wherein said body of laminated composite structure is cellular.

5. The method according to claim 1 wherein said radiation carrier is an optical fiber.

6. The method according to claim 1 wherein said radiation carrier is an optical glass rod.

* * * * *